(12) United States Patent
Knorr

(10) Patent No.: US 8,904,874 B2
(45) Date of Patent: Dec. 9, 2014

(54) ULTRASONIC TRANSMITTING AND RECEIVING DEVICE FOR THICKNESS AND/OR GRAMMAGE MEASUREMENT

(76) Inventor: Helmut Knorr, Utting Am Ammersee (DE)

( * ) Notice: Subject to any disclaimer, the term of this patent is extended or adjusted under 35 U.S.C. 154(b) by 332 days.

(21) Appl. No.: 13/431,171

(22) Filed: Mar. 27, 2012

(65) Prior Publication Data

US 2012/0247212 A1    Oct. 4, 2012

(30) Foreign Application Priority Data

Mar. 28, 2011   (DE) .......................... 10 2011 015334

(51) Int. Cl.

| | | |
|---|---|---|
| *G01N 29/04* | (2006.01) | |
| *B29C 47/92* | (2006.01) | |
| *B29C 47/00* | (2006.01) | |
| *G01B 17/02* | (2006.01) | |
| *G01N 33/34* | (2006.01) | |

(52) U.S. Cl.
CPC ....... *G01B 17/02* (2013.01); *B29C 2947/92942* (2013.01); *B29C 2947/92447* (2013.01); *B29C 2947/92152* (2013.01); *B29C 47/92* (2013.01); *B29C 2947/92647* (2013.01); *B29C 47/0009* (2013.01); *G01N 33/346* (2013.01)
USPC .......................................................... 73/632

(58) Field of Classification Search
USPC .......... 73/632, 1.82, 159, 579, 597, 589, 602, 73/627, 628, 630
See application file for complete search history.

(56) References Cited

U.S. PATENT DOCUMENTS

| | | | | |
|---|---|---|---|---|
| 4,117,732 | A | * | 10/1978 | Brazhnikov .................... 73/599 |
| 4,446,735 | A | | 5/1984 | Weilacher |
| 4,669,312 | A | * | 6/1987 | Maurer ........................... 73/600 |
| 4,730,473 | A | * | 3/1988 | Rottlander et al. ............ 72/12.7 |
| 5,077,478 | A | * | 12/1991 | Walford ..................... 250/359.1 |
| 5,621,173 | A | | 4/1997 | Knorr |
| 5,922,960 | A | * | 7/1999 | Toda ............................... 73/597 |
| 7,191,655 | B2 | * | 3/2007 | Matsuzawa ..................... 73/579 |
| 7,748,274 | B2 | * | 7/2010 | Pellaton et al. ................. 73/649 |
| 8,448,517 | B2 | * | 5/2013 | Itsumi et al. .................... 73/597 |
| 2007/0034008 | A1 | | 2/2007 | Voss |

FOREIGN PATENT DOCUMENTS

| | | |
|---|---|---|
| DE | 3048710 A1 | 7/1982 |
| DE | 4236436 A1 | 7/1994 |
| DE | 19908932 A1 | 12/1999 |
| DE | 20109119 U1 | 8/2001 |
| DE | 20312388 U1 | 11/2003 |
| DE | 10327389 B3 | 12/2004 |
| DE | 202005010037 U1 | 9/2005 |
| DE | 102005037086 A1 | 2/2007 |

* cited by examiner

*Primary Examiner* — J M Saint Surin
(74) *Attorney, Agent, or Firm* — The Eclipse Group LLP

(57) ABSTRACT

An ultrasonic transmitting and receiving device is provided for measuring the transmission and/or reflection of ultrasonic waves on a thin material sheet, in particular on a foil sheet. The device may include a plurality of ultrasonic transmitters, a plurality of ultrasonic receivers, wherein the number of the ultrasonic transmitters corresponds to the number of the ultrasonic receivers, and one receiver electronics respectively for each of the ultrasonic receivers or each a group receiver electronics respectively for a predetermined number of ultrasonic receivers. A method is provided for ultrasonic absorption and/or transmission measurement, in which signals are emitted by multiple ultrasonic transmitters at the same time or nearly at the same time which are received by ultrasonic receivers and in which the received signals are evaluated in parallel.

19 Claims, 4 Drawing Sheets

ULTRASONIC TRANSMITTING AND RECEIVING DEVICE FOR THICKNESS AND/OR GRAMMAGE MEASUREMENT

RELATED APPLICATIONS

This application claims the benefit of German patent application No. DE 10 2011 015 334.9 filed Mar. 28, 2011, the content of which is incorporated by reference herein in its entirely.

TECHNICAL FIELD

The invention relates to an ultrasonic transmitting and receiving device for measuring the transmission and/or reflection of an ultrasonic signal on a material sheet (material foil). Based on the transmission and/or reflection measurement, the layer thickness and/or the grammage (mass per unit area) of the material sheet can be absolutely determined.

BACKGROUND

From DE 42 36 436 A1, a measurement method for contact-less determination of the grammage of thin material sheets by means of ultrasonic sound is known. In the method, by means of an ultrasonic transmitter and an ultrasonic receiver, the transmission absorption of an ultrasonic beam upon passage through a material foil is determined in contact-less manner. Based on the absorption and a calibration factor, the grammage is calculated.

From DE 201 09 119 U1, a further device for measuring the thickness of material sheets is known. There, the material sheet is pulled over a roller, wherein a sensor is arranged on a rolling cart moving back and forth over the roller in traversing manner for thickness measurement.

Further ultrasonic sensor arrangements for grammage determination or for grammage comparison are known from DE 103 27 389 B3, DE 199 08 932 A1, DE 10 2005 037 086 A1, DE 203 12 388 U1 and DE 30 48 710 A1.

There is a need for providing an ultrasonic transmitting and receiving device, an arrangement including the device as well as a method, in which the thickness measurement and/or grammage measurement on a material sheet are improved.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, an ultrasonic transmitting and receiving device is provided, by which the transmission and/or the reflection of the ultrasonic waves through or from a thin material sheet are measured by means of the ultrasonic waves. The thickness and/or the grammage (mass per unit area) of the material sheet may be determined based on the measured transmission and/or reflection. The device comprises a plurality of ultrasonic transmitters, wherein each of the ultrasonic transmitters is oriented such that an ultrasonic signal can be emitted towards a thin material sheet. The ultrasonic signal may be a signal pulse or a sequence of signal pulses ("signal burst"). The device unit may include a control unit, by means of which the absolute layer thickness and/or the grammage can be calculated using a calibration value or a calibration curve and the measured transmission and/or reflection and can be displayed and/or output as an absolute value.

An ultrasonic receiver may be associated with each of the ultrasonic transmitters and oriented towards this such that the ultrasonic signal emitted by the associated ultrasonic transmitter can be received. For example, for determining the transmission, the receiver may be arranged on the side of the material sheet opposing the ultrasonic transmitter and oriented towards the ultrasonic transmitter. For example, for measuring the reflection, either a separate receiver may be arranged on the same side of the material sheet as the ultrasonic transmitter, or the ultrasonic transmitter may operate as a transceiver, by which the signal can be both radiated and received.

Dedicated receiver electronics may be associated with each of the ultrasonic receivers, or group receiver electronics may each be associated with a group of ultrasonic receivers, such that parallel processing of the ultrasonic signals received and converted by the ultrasonic receivers can be executed with the receiver electronics or group receiver electronics. Within the group receiver electronics a dedicated electronics unit may be associated with each ultrasonic receiver in the group of the ultrasonic receivers which are associated with the group receiver electronics, such that parallel processing of the received voltage signal converted by the receiver can also be executed for each member of the group.

By the plurality of ultrasonic transmitters, ultrasonic receivers and receiver electronics or group receiver electronics, it is provided to emit, to receive ultrasonic signals and to at least partially condition or process them by the electronics in time-parallel manner. Therefore, it is possible to substantially increase the spatial density and/or the repetition rate of the transmission and/or reflection measurements on the material sheet as compared to for example a reversing system with only one transmitting/receiving unit. Thereby, for example, the quality control by means of thickness and/or grammage determination on a material sheet can be substantially improved. For example, thereby, the fault detection in a material sheet such as a fuel cell membrane, battery membrane or the like increases such that the reject rate is considerably decreased related to the entire production process due to the fault detection of material defects.

The ultrasonic transmitters may be arranged so as to be distributed on a supporting device such that they extend in transverse direction to the material sheet. Thereby, it is no longer required to provide a traversing device moving the ultrasonic transmitters back and forth across the width (transverse direction) of the material sheet. The ultrasonic transmitters may be fixedly arranged, i.e. they are moved neither in transverse direction nor in longitudinal direction to the material sheet, i.e. during the measurements, exclusively the material sheet moves in longitudinal direction. Thereby, the expenses for providing mechanically moving parts are reduced or are completely avoided. In an embodiment, it can be provided that the supporting device for the ultrasonic transmitters is moved over a small transverse stroke, for example a transverse stroke of less than $1/10$, $1/15$, $1/20$ or $1/30$ of the material sheet width.

In an embodiment, the ultrasonic transmitters are arranged so as to be spatially distributed both over the transverse direction of the material sheet and over a predetermined depth in longitudinal direction of the material sheet. By the distribution of the ultrasonic transmitters in longitudinal direction, it becomes possible to achieve the coverage of the measurement points in longitudinal direction of the material sheet with temporal repetition in nearly continuous or even overlapping manner in a clocked, non-continuous measurement even at high sheet longitudinal velocities. Alternatively or additionally, it is possible to increase the resolution of the measurement locations in transverse direction with both transverse and longitudinal offset of the adjacent ultrasonic transmitters such that complete or nearly complete coverage with measurement points in transverse direction is achieved.

Notably, multiple lines of ultrasonic transmitters extending in transverse direction of the material sheet may be provided, wherein all of the ultrasonic transmitters of a line are offset to each other in transverse direction and the lines are offset to each other in longitudinal direction. Therein, the dual offset is advantageous such that with projection of the ultrasonic transmitters in longitudinal direction, thus upon viewing the ultrasonic transmitters in the direction of the running direction of the material sheet, the projection of the ultrasonic transmitters is arranged equidistantly to each other. Therein, viewed in projection and in transverse direction, a uniform sampling density in transverse direction of the material sheet is achieved. In an alternative or additional embodiment, a sequence of the ultrasonic transmitters results in a projection in longitudinal direction such that a repeating permutation of the line number of the associated ultrasonic transmitter arises in projected sequence in transverse direction. (Example for illustration: if the lines and columns result in a skewed array or a skewed matrix $A_{ij}$ of the size 3×3 with the column number i=1, 2, 3 and the line number j=1, 2, 3, then the permutation sequence $a_{11}$, $a_{12}$, $a_{13}$, $a_{21}$, $a_{22}$, $a_{23}$, $a_{31}$, $a_{32}$, $a_{33}$ results in longitudinal projection). With such an arrangement, the ultrasonic transmitters can be arranged next to each other on a small area in compact manner, while the coverage with ultrasonic transmitters (and the ultrasonic signals radiated by them to the material sheet, respectively) projected in longitudinal direction is provided in transverse direction to the material sheet in continuous or nearly continuous manner.

The ultrasonic transmitters may be arranged such that only each one ultrasonic transmitter is located in longitudinal direction of the moving material sheet, i.e. all of the ultrasonic transmitters are offset to each other in transverse direction. However, this does not mean that the active transmitting surfaces of the ultrasonic transmitters do not overlap in longitudinal projection (see below). If for example two lines of ultrasonic transmitters with ultrasonic transmitters arranged as distributed over the transverse direction are provided and if the two lines are offset in longitudinal direction, thus, advantageously, the ultrasonic transmitters of the second line are arranged offset by half the distance of the ultrasonic transmitters of the first line in transverse direction with respect to the ultrasonic transmitters of the first line. Thereby, in longitudinal projection, each of the ultrasonic transmitters of the second line is located between two ultrasonic transmitters of the first line (except for the last ultrasonic transmitter of the second line).

According to an embodiment, the device includes multiple lines of ultrasonic transmitters arranged to be offset to each other in longitudinal direction, wherein the ultrasonic transmitters of the same column are located on one line in the lines located one behind the other, which is under an angle with respect to the longitudinal direction of the material sheet. In some implementations, the angle of this line is in a range of 10° to 80° to the longitudinal direction, or in other implementations in a range of 20° to 70°, 30° to 60° or 40° to 50°.

Each of the ultrasonic transmitters may have an active transmitting surface extending both in longitudinal direction and in transverse direction. In some implementations, the transmitting surface of the ultrasonic transmitters is round or elliptical. In an embodiment, the ultrasonic transmitters are arranged such that in projection of the ultrasonic transmitters in longitudinal direction of the material sheet, the transmitting surfaces of the ultrasonic transmitters lying next to each other in transverse direction overlap. Thereby, seamless coverage of the sampling of the material sheet in transverse direction in projection is achieved. In some implementations, the overlapping degree between each two ultrasonic transmitters adjacent in projected transverse direction is at least 10% in transverse direction of the projected transmitting surface, or in other implementations at least 15%, 20%, 30%, 35% or 40%.

In some implementations, 100% of the sheet width is covered by means of the ultrasonic transmitters or the ultrasonic beam emitted by the ultrasonic transmitters, and in some implementations at least partially overlapping coverage in transverse direction of the material sheet is achieved.

A sensor unit of the device is composed of an ultrasonic transmitter and one or two ultrasonic receivers associated with the ultrasonic transmitter (two receivers in case of the simultaneous measurement of transmission and reflection). The radiating direction of the ultrasonic signal from the ultrasonic transmitter towards the surface may be perpendicularly or approximately perpendicularly oriented to the material sheet. The receiver of the sensor unit therein may be oriented such that it is arranged opposing the ultrasonic transmitter with respect to the material sheet in transmission and receives the transmitted signal. Alternatively or additionally, the ultrasonic receiver measuring the reflection is arranged on the same side of the material sheet as the ultrasonic transmitter. The ultrasonic receiver may at the same time be the ultrasonic transmitter.

If both transmission and reflection are measured, then in some implementations, one dedicated receiver electronics is provided for each of the reflection receivers and transmission receivers or one group electronics is provided each for a group of reflection receivers and transmission receivers. The described parallel processing of the received signals therein relates to both the transmission and the reflection signals. In the processing or calculation the quotients of the transmission and reflection signals may each be processed for each sensor unit (transmitter and associated transmission and reflection receivers) (quotient either T/R or R/T).

In an embodiment, the ultrasonic receivers are arranged on a second supporting device paired to the arrangement of the ultrasonic transmitters on the first supporting device. In transmission measurement, the second supporting device may be arranged on the side of the material sheet opposing the first supporting device for the ultrasonic transmitters. By the arrangement of the receivers on a common, second supporting device, all of the receivers can be collectively oriented to the ultrasonic transmitters such that individual orientation of each receiver to its associated transmitter is not required.

Each of the receiver electronics or group receiver electronics may include an amplifier, in which the amplification is adjustable. In particular, each of the amplifiers may be adjustable in multiple amplification stages and/or the amplification of each of the amplifiers is individually, but centrally adjustable under control of a main control unit via the control or programming of the main control unit. By means of the adjustable amplification, the basic amplification for the amplification of the received ultrasonic signal converted to a voltage signal can be calibrated for each of the ultrasonic receivers. Thereby, for example, an amplification of the received signal is adjusted such that the same signal (for example same signal amplitude and/or signal voltage) is present with all of the amplified signals on identical measurement conditions. Such a uniform or identical measurement condition for example exists if no material sheet is provided between transmitter and receiver or in reflection arrangement towards the radiated signal such that a basic signal in air (transmission signal/reflection signal against air) results in a uniform signal strength after amplification. In some implementations, even when using the group receiver electronics the amplification is also individually adjustable for each individual ultrasonic receiver of the group. Thereby, differences in the transmitting strength of the ultrasonic transmitters, the receiver sensitivities of the signal receivers or different attenuations on the signal paths can be normalized.

The receiver electronics or the group receiver electronics may have a microcontroller, in particular a microcontroller, by which or in which the amplification of the amplifier of the receiver electronics is adjustable. This correspondingly applies to the group receiver electronics. Here too, the amplification again may be individually and independently adjustable for each of the ultrasonic receivers of the group.

Alternatively or additionally, each of the receiver electronics or the group receiver electronics includes a signal processor for evaluating the signal or signals received by the associated ultrasonic receiver or the group of ultrasonic receivers. With the signal processor, it is possible to provide signal processing on the level of the receiver electronics or group receiver electronics such that parallel processing is implemented. The signal processor in the group receiver electronics may have a processing speed for processing the signals of the ultrasonic receivers of the group in parallel or sequentially. For example with clocked measurement the evaluation or calculation for each receiver of the group is terminated before a new measurement clock begins. Alternatively, a dedicated signal processor is provided or implemented for each of the receivers of the group in the group receiver electronics.

A main control unit may be provided, by means of which a transmit signal can be generated, which is supplied to each of the ultrasonic transmitters via a bus line or parallel lines. In particular the signal generation and signal transmitting connection between the main control unit and the ultrasonic transmitters is such that the ultrasonic transmitters radiate the ultrasonic signal at the same time or with a slight temporal offset. If a temporal offset is present, then in clocked measurement operation the period of time between the earliest ultrasonic signal emitted by one of the ultrasonic transmitters to a time, at which the last ultrasonic transmitter emits the signal in the same measurement clock, is smaller than the propagation time of undesired sound reflections and/or propagation times between an ultrasonic transmitter and a signal receiver not associated with this ultrasonic transmitter (i.e. from an ultrasonic signal passing between different sensor units).

Besides the ultrasonic transmitter and receiver pairs, a measuring group (in the following also referred to as a "sensor unit") with at least one signal transmitter and a signal receiver may be associated with the device, by which the layer thickness and/or the grammage (mass per unit area) of the material sheet can be determined during a reversing movement or reciprocation of the measuring group transversely to the material sheet. In the sensor unit, a sensor for detecting transmission and/or reflection values of the material sheet is movable in transverse direction of the material sheet transported in longitudinal direction. The sensor unit can be moved back and forth in traversing manner along the device (for example between the outer longitudinal edges of the material sheet) by means of a drive unit. Thereby, for example, during a production process of the material sheet, the transverse distribution of the layer thickness and/or the grammage is monitored (e.g. along a zigzag-shaped measuring path along the material sheet).

The device may include a sensor calibration position, in which the sensor unit is moved out of the material sheet measuring section. In the sensor calibration position, a supporting device with a calibration sample (as a calibration standard) is arranged. In the sensor calibration position, the sensor is moved relatively to the calibration sample and/or the calibration sample is moved relatively to the sensor by means of a drive.

In an embodiment, a rotation and/or linear movement is effected by means of a rotation and/or linear drive, which moves the calibration measurement sample retained in the supporting device relatively to the sensor. Additionally or alternatively in the sensor calibration position the sensor can be moved over the calibration sample retained in the supporting device planar or at least in a linear direction, which in some implementations is preferably in the transverse direction of the material sheet.

The sensor unit may include an ultrasonic sensor unit, in which the measurement signal for layer thickness and/or grammage determination is an ultrasonic pulse. Alternatively, an optical sensor is used, which for example uses a laser beam or a light emitting diode beam. Further alternatively, the sensor unit may have a ray sensor emitting and receiving gamma or beta rays.

In an embodiment, the sensor unit is exclusively constructed as a transmission unit, in which only the absorption in transmission of the sensor signal through the material sheet is determined. Or the sensor unit is exclusively a reflection unit, in which the reflection of the measurement signal from the material sheet or from the backside of the material sheet is detected. Or alternatively, the sensor unit is a combined transmission and reflection measurement unit, in which both the attenuation of the sensor signal in reflection and in transmission are determined. In such a transmission and reflection measurement, one of the values can be used for plausibility check of the other value and/or for averaging in the layer thickness and/or grammage determination.

The sensor unit may be used for calibration of the plurality of the ultrasonic transmitter and receiver pairs of the device and/or the sensor unit may be calibrated in the sensor calibration position with the calibration sample.

According to another implementation, an arrangement includes a device according to one of the preceding embodiments and an extruder, in which an actuator of an extrusion die of the extruder is adjustable depending on the layer thickness and/or grammage measurement of the device. Thereby, control of the layer thickness or of the grammage in the manufacture of a material sheet, for example a foil sheet, is provided.

According to another implementation, an ultrasonic transmitting and receiving device with a plurality of sensor units is used, wherein each sensor unit is formed of an ultrasonic transmitter and an ultrasonic receiver associated with it. The device may be formed as above described, i.e. the above described elements can also be used individually or in any combination with each other in the device for the method.

In the method, a control signal is supplied to all of the ultrasonic transmitters at the same time or with a little temporal offset within a time window such that the ultrasonic transmitters emit their ultrasonic signal at the same time or within the time window. The time window is dimensioned such that a spurious reflection signal and/or a signal of another ultrasonic transmitter is not received by an ultrasonic receiver associated with the ultrasonic transmitter in a corresponding time window of the measurement of the ultrasonic signal. By the simultaneous or nearly simultaneous transmission of the ultrasonic signal, parallel measurement of all sensor units is provided, wherein at the same time cross-talk between the sensor units or an error signal by reflection within the measuring section of a sensor unit is excluded.

Furthermore, in the method, a parallel or substantially parallel processing is provided, wherein one receiver electronics is associated with each of the ultrasonic receivers or one group receiver electronics is associated with a group of ultrasonic receivers, by which evaluation or pre-processing of the signals of the ultrasonic receivers can be executed in parallel or substantially in parallel. Using the group receiver electronics the processing may also be effected for all of the signals of the receivers associated with the group or by fast electronics such that in a clocked measurement the processing result for all of the receivers of the group is finished before the next measurement clock occurs.

The evaluated or pre-processed signals may be supplied to the receiver electronics or the group receiver electronics of a main control device. Evaluation of the signal for determining the thickness and/or grammage determination may be effected either already on the level of the receiver electronics or group receiver electronics or in the main control device after forwarding the pre-processed signals to the main control device.

Thereby, by means of the method, both parallel emission (multiple measurement positions on the material sheet at the same time) and parallel processing of the signals is provided such that an intensive detection of the thickness and/or the grammage of a material sheet is provided with high density and repetition rate.

In an embodiment, the sensor units are calibrated by measuring a basic sensitivity based on a signal transmitted through the air (thus without material sheet). This value may be used in determining the sensitivity in order to adjust an amplification factor individual to the transmitting unit in the receiver electronics or group receiver electronics such that a receive signal is obtained after amplification with identical conditions on the measuring section, which has the same size or strength normalized for all transmitting units.

Alternatively or additionally, a calibration and detection of a conversion factor between transmission value and/or reflection value and association with a thickness and/or a grammage of a material sheet is effected by using the calibration at a calibration sample or calibration standard, which is applied between the sensor units such that measurement on a material sheet is simulated. After removal of the calibration sample a corresponding material sheet to be measured can then be interposed between the sensor units, the measurements on the material sheet can be carried out and the thickness and/or the grammage can be assigned by means of the previously determined calibration value.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 1:
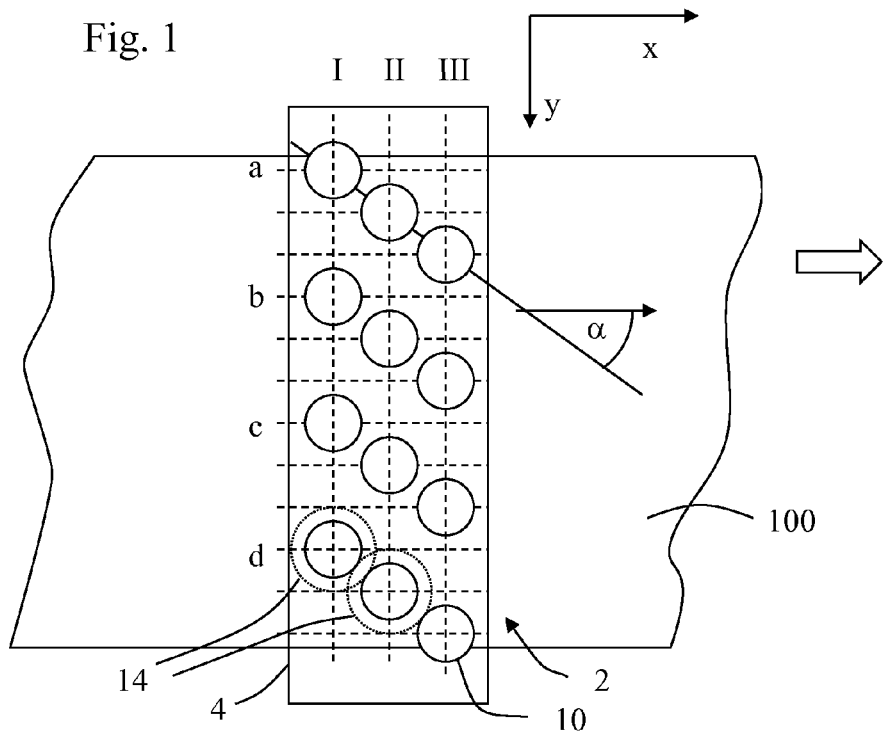
FIG. 1 is a schematic plan view of a measuring unit for measuring the grammage of a material sheet.

FIG. 1 shows in schematic plan view a measuring unit 2 for thickness measurement and/or grammage determination at a material sheet 100. In the measuring unit, a plurality of ultrasonic transmitters 10 and an equal number of ultrasonic receivers 12 in the form of an array are arranged planar above the material sheet (in the illustrated example, the ultrasonic transmitters 10) and below the material sheet (in the illustrated example, the ultrasonic receivers 12). For simplicity, the transporting device for moving the material sheet 100 forward in the longitudinal direction x thereof is not represented. In the figures, the size ratios and distance ratios are not represented to scale, but are presented such that they serve for explaining the invention.

Figure 2:
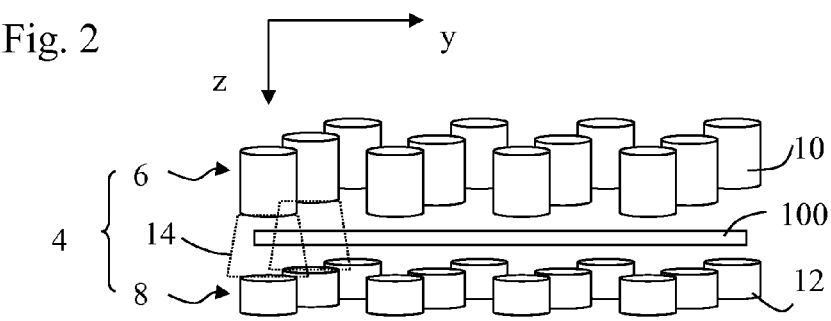
FIG. 2 is a schematic side view of the ultrasonic transmitters and receivers of the measuring unit above and below the material sheet.

FIG. 2 shows in schematic and partially perspective representation the distribution of the ultrasonic transmitters 10 and the ultrasonic receivers 12 arranged correspondingly opposite and coaxial to each of the ultrasonic transmitters.

Figure 3:
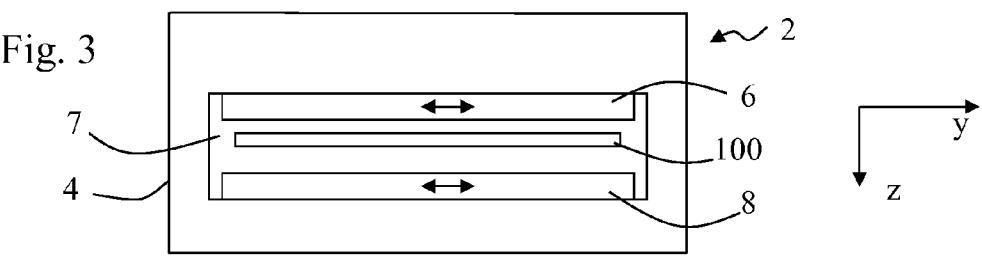
FIG. 3 is a schematic side view of the measuring unit with the transmitting block arranged above the material sheet and the receiving block arranged below the material sheet.

FIG. 3 shows in schematic lateral view a portal 4 of the measuring unit 2 with an upper transverse beam and a lower transverse beam as well as the lateral pillars, which together leave open a slot 7 extending in x direction through the portal 4. The material sheet 100 is transported in x direction through the slot 7. The portal and thus the array arrangement extends transversely, thus in y direction, to the material sheet 100.

FIG. 1 indicates by means of the circles, which represent the ultrasonic transmitters 10, how the ultrasonic transmitters form three lines I, II and III, wherein each line is offset in x direction to the preceding one. The columns of the array are formed by the columns a, b, c and d. The ultrasonic transmitters 10 are not on a straight line in x direction, but are arranged offset to each other in an angle α to the x direction. An ultrasonic receiver 12 is oriented coaxially in z direction to each of the ultrasonic transmitters 10. Thus each one of the ultrasonic sensors is formed by one of the ultrasonic transmitters and one paired ultrasonic receiver, which is arranged in the direction of the normal perpendicularly to the center of the sound emitting surface of the ultrasonic transmitter. I.e. in a sensor, the center of the receiving surface of an ultrasonic receiver 12 is oriented coaxially to the axis of a transmitter 10. Thereby, a pairing of ultrasonic transmitter and ultrasonic receiver respectively results, wherein 4×3=12 ultrasonic transmitting/receiving pairs are provided in the example illustrated in the figures.

Both the number of the lines I, II and III and the number of the columns a, b, c, d can be selected differently depending on the material sheet width and the desired overlap or the distance of the measurement regions (see below). The ultrasonic transmitters 10 are mechanically supported distributed in planar manner on a transmitting block 6, wherein the transmitting block 6 in turn is mounted on the upper transverse beam of the portal 4. Furthermore, FIG. 3 shows a receiving block 8 below the material sheet 100 on which the ultrasonic receivers 12 are supported distributed in planar manner, wherein here the receiving block 8 is mounted on the lower transverse beam of the portal 4. In an embodiment, it can be provided that both the transmitting block 6 and the receiving block 8 are displaced synchronously with each other in reversing manner in transverse direction (y direction), while the material thickness or the grammage is measured. By this optional transverse displacement it is effected that the non-uniform signal distribution of the ultrasonic signal is drawn over various "tracks" in x direction of the material sheet in a temporally varied manner. In a synchronous, harmonic transverse displacement of the blocks 6, 8, thus, there results a sinusoidal extension of the measurement points in x direction of the material sheet. The reversing, synchronous displacement of the blocks 6, 8 is effected such that the coaxial orientation of the ultrasonic transmitters 10 to the ultrasonic receivers 12 is maintained. However, the blocks 6 and 8 are preferably rigidly supported on the portal 4 or on a frame of the measuring unit 2.

In the schematic side view of FIG. 2 and the plan view of FIG. 1, the extension of the main intensity cone 14 of an ultrasonic signal distribution is illustrated. Therein, the signal lobe 14 illustrates the lateral divergence of an ultrasonic wave of the ultrasonic signal, which is radiated from an ultrasonic transmitter 10. The diameter of the lobe 14 is greater than the diameter of the radiation surface of the ultrasonic transmitter 10 on the level of the receiving surface of the ultrasonic receivers 12. As indicated by means of the dotted circles 14 in FIG. 1, the distance between the adjacent ultrasonic transmitters 10 is selected such that each ultrasonic receiver 12 substantially only receives the main intensity of the ultrasonic signal of the ultrasonic transmitter 10 associated with and opposing it. Thereby, interferences or cross-talk of a transmitter/receiver pair with the other transmitter/receiver pair (between the sensors) is minimized.

The angular offset a of the transmitter/receiver pairs of the columns relative to the x direction allows performing the grammage determination in y direction in at least a partially overlapping manner such that in ideal case the thickness and/or grammage distribution of the material sheet 100 over the entire width of the material sheet is possible at each time. This arrangement thus substantially differs from that known from the above cited DE 201 09 119 U1, in which—due to the traversing operation of the ultrasonic transmitter—the detection of a material sheet defect (thickness and/or grammage deviation) rather is left to the statistical coincidence than a systematic measurement as it is allowed with the present invention.

Figure 4:
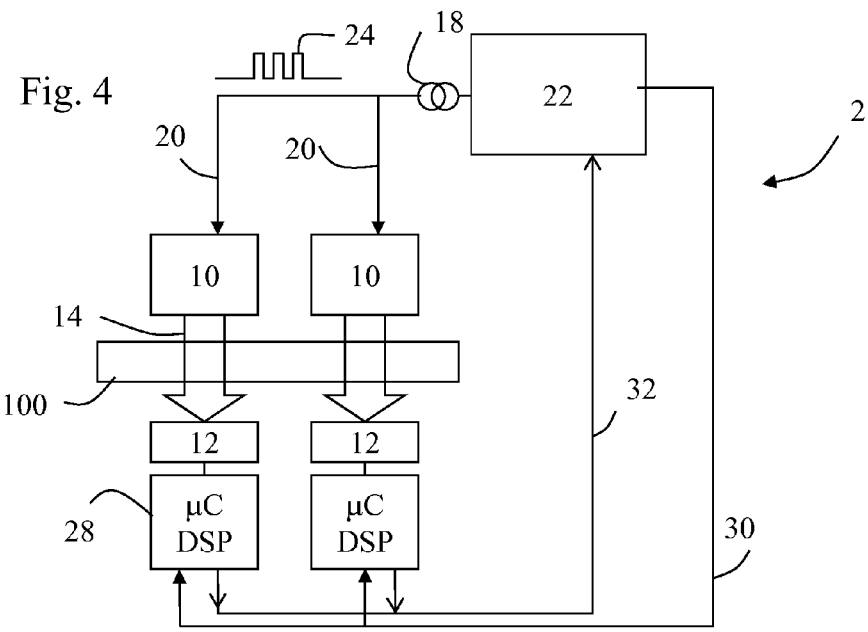
FIG. 4 is a block diagram of the transmitting, receiving and control unit of the measuring unit.

FIG. 4 shows in block diagram manner the construction of the measuring unit 2. Here, only two of the ultrasonic transmitters 10 and ultrasonic receivers 12 are exemplarily illustrated. The ultrasonic signal 14 propagates from the transmitter 10 towards the material sheet 100, passes it with attenuation of the intensity of the signal, which impinges on the receiving surface of the receiver 12 after exiting on the bottom of the material sheet. In each measurement interval (time window G in FIG. 6), the signal illustrated as a signal sequence 24 in FIG. 4 is supplied to each transmitter. The signal sequence 24 is generated in a main control unit 22 and supplied to the ultrasonic transmitters 10 in parallel or simultaneously via a transducer 18.

The ultrasonic signal 14 converted into an electrical signal by the ultrasonic transducer of the ultrasonic receivers 12 is supplied to a receiver controller 28. A dedicated controller 28 is associated with each ultrasonic receiver 12. The electrical signal is processed by means of a digital signal processor in the receiver controller 28 such that just on the level of the controllers 28 signal pre-processing is executed. The signal processing may be effected by means of corresponding calibration values such that the controllers 28 may output a signal value corresponding to the material thickness or the grammage to the control unit 22 via a receive signal line 32. Thereby, the main control unit 22 is relieved from the individual signal conditioning or processing and only statistical and control tasks have to be executed by the control unit 22. By the parallel processing in the controllers 28 respectively associated with a receiver 12, a parallel processing is provided, which together with the planar distribution of the sensor units 10, 12 in the array allows a nearly complete "in situ" monitoring of the material quality of the material sheet 100. Even in fast production processes for the material sheet, thereby, high-speed quality monitoring of high density is made available such that high-quality material sheets (such as electrolyte membranes, fuel cell membranes or high-performance battery isolator foils or membranes) can also be produced and the quality thereof can be monitored online.

Figure 5:
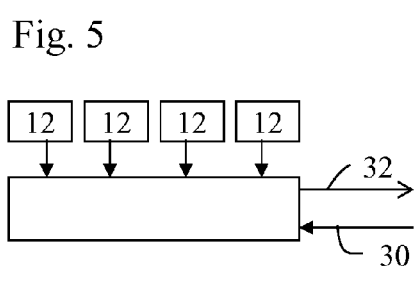
FIG. 5 schematically shows a group of ultrasonic receivers and the group controller associated therewith.

FIG. 5 shows a further embodiment, in which a group controller 29 is provided for each four receivers 12 instead of each one controller 28 per receiver 12. In the 3×4 array of FIG. 1, then, three group controllers 29 are used instead of twelve individual controllers 28. The group controllers have a dedicated amplifier component with individual amplification for each receiver 12 belonging to the group. By means of the signal processor DSP of the group controller 29, the signals of the associated receivers 12 are evaluated sequentially one after the other, but with such a velocity that the computing result is available and output before the next measurement interval begins. With respect to FIG. 6 this means that the result of the signal evaluation of all of the associated receivers 12 is transmitted to the main control unit before the next time window G starts (the evaluation period of time is thus shorter than the sum of the periods of time G and U). Programming of the amplification, the supply of the supply voltage(s) of the controller 29 and programming of the signal processor DSP of the controller 29 are effected via the control line 30 coming from the main control unit 22. The evaluation signals of the controller 29 are supplied to the main control unit 22 via the line 32.

Figure 6:
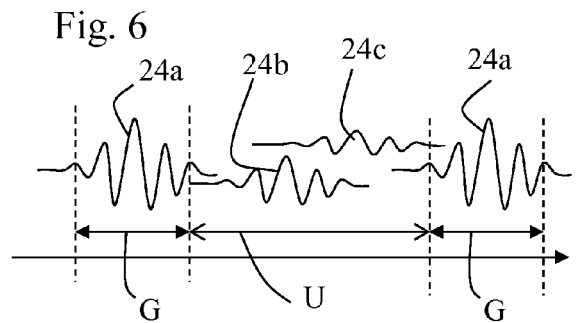
FIG. 6 is a time diagram with received signals and measurement time windows.

The time diagram of FIG. 6 illustrates the voltage signal at the output of the receivers 12. The measurement is performed with the repetition rate 1/(G+U), thus also with this rate, the signal sequence 24 is output to the transmitters 10. Therein, G is the time window or the time gate, in which the received signal 24a is evaluated in order to determine from it the thickness and/or the grammage of the material sheet by means of the DSP. U is a time interval or a period of time, during which the ultrasonic signal is not received and processed. The duration of G is dimensioned such that the evaluation can be performed with an error as low as possible (multiple wave trains after excitation with the pulse burst 24). The duration of U is dimensioned such that undesired spurious signals are masked in this time. Here, exemplarily illustrated spurious signals are a reflection signal 24b, which arises in that the signal radiated from the transmitter surface is partially reflected on the material sheet surface, returns to the transmitter surface, is again reflected there and again passes the material sheet and is recorded by the receiver 12 with corresponding propagation time delay. A further spurious signal 24c arises in that the transmit signal is radiated by a transmitter 10 laterally towards an adjacent receiver 12 and there in the adjacent receiver induces a signal 24c which is propagation time-delayed but weaker.

Figure 7:
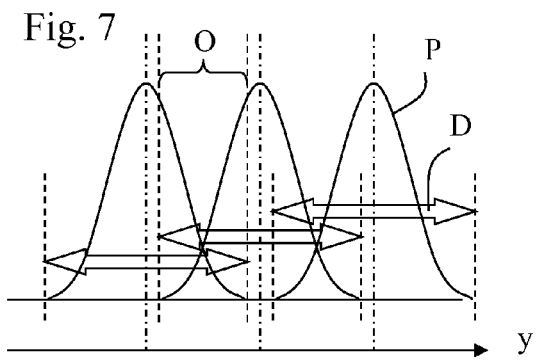
FIG. 7 is a set of intensity profiles of the ultrasonic signals emitted by the ultrasonic transmitters in projection.

FIG. 7 shows in x projection the ultrasonic signal intensity extending in y direction until it results by the array of the transmitting/receiving pairs across the width of the material sheet. In FIG. 7, for simplicity, only 3 of the overall 12 intensity curves P are illustrated. Therein, the intensity P is that of one transmitter 10, respectively. Therein, the intensity curve is approximately Gaussian, and with respect to the z axis there is rotational symmetry of the intensity distribution because the ultrasonic transmitting surfaces are round and radiate in rotationally symmetric manner.

As is apparent from FIG. 7, the maximum diameter ranges of the diameter D of the radiation surfaces of the ultrasonic transmitters 10 overlap in x projection such that an overlapping region O results in the transmitter 10 closest in y direction. Thereby, the measurement intensity P of all transmitters 10 never drops to 0 in the extension of the y direction, and in transverse direction (y direction) of the material sheet 100, a width region does not arise, which is not covered by the measurement or the ultrasonic signal. Therefore, due to the array and the columns of the array arranged in an angular offset, a dead zone in transverse direction of the material sheet does not arise.

Figure 8:
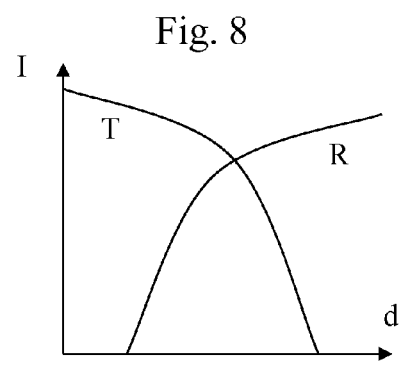
FIG. 8 is a plot of the intensity of the ultrasonic signal in transmission and reflection depending on the thickness of the material sheet.

FIG. 8 schematically shows the intensity curve of an ultrasonic signal in transmission T and in reflection R depending on the thickness d of the material sheet. Based on such calibration curves for an ideal material sample the thickness or the grammage can be determined based on the actually measured signal variation. In the illustrated arrangement, measurement is made in transmission such that the curve T is used in the thickness or grammage determination.

For example, if a thicker or thinner material sheet would result in an intermediate region between the intensity maxima of the intensity curve P of two transmitters 10 adjacent in y direction in the material sheet to be measured due to a systematic production fault, thus, this systematic fault can be identified either by detecting systematically a deviating value in the two concerned transmitter/receiver pairs 10/12. Or, alternatively, as described in connection with FIG. 3, the transmitting block and the receiving block 6, 8 are displaced synchronously with a short y stroke in y-direction such that the measurement sensitivity is shifted towards maximum of the intensity curve P with such a systematic fault.

Figure 9:
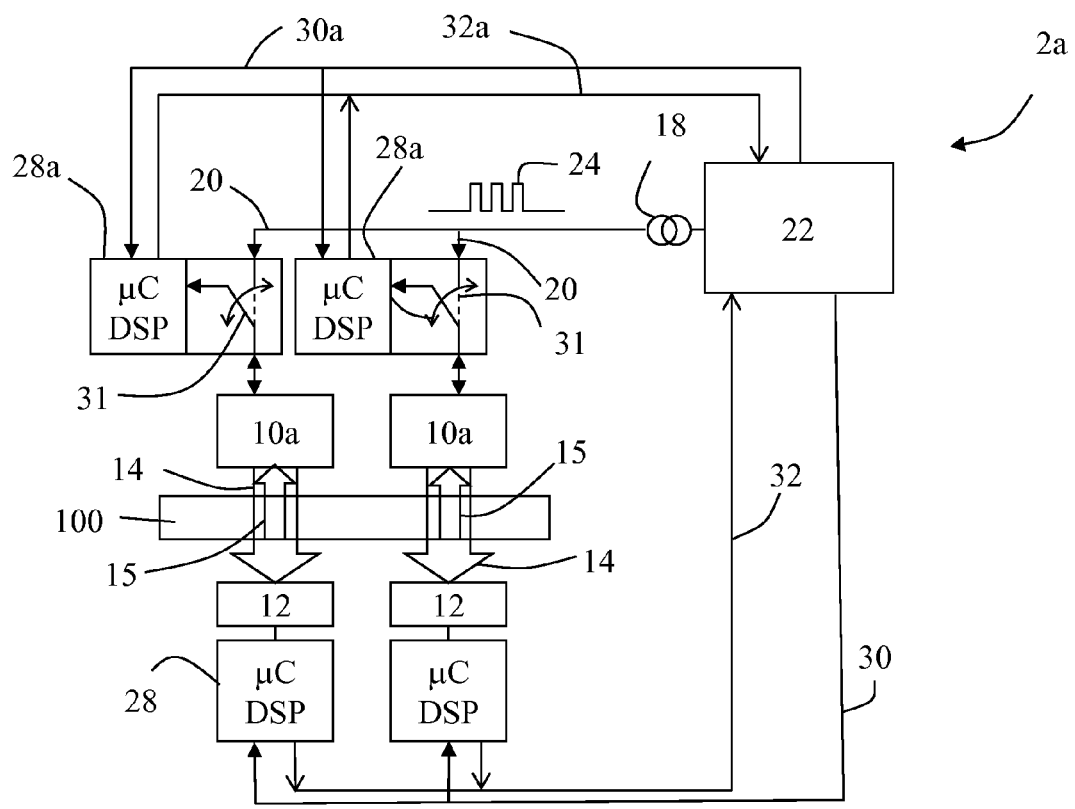
FIG. 9 is a block diagram of the transmitting, receiving and control unit in further embodiment of the measuring unit.

FIG. 9 shows a further configuration of the measuring unit 2 as a measuring unit 2a. Identical, same or equivalently acting elements of the measuring unit 2a are labeled with the same reference characters or with reference characters supplemented with the addition "a" as the corresponding element of the measuring unit 2. In the measuring unit 2a, the reflection signal 15 reflected back from the material sheet 100 towards the ultrasonic transmitter 10 can also be evaluated or is evaluated with respect to the reflection R (cf. FIG. 8).

The unit 2a allows the following measurement modes: transmission measurement, reflection measurement, transmission and reflection measurement and additionally to these or alternatively to these a propagation time measurement for direct thickness calculation.

With respect to the transmission measurement, the setup is as described above with respect to FIGS. 1 to 8. For reflection measurement, the ultrasonic transmitter 10a operates as a transceiver receiving the ultrasonic signal 15 reflected on the material sheet 100 and converting it into a voltage signal. First, the signal sequence 24 generated by the main control unit 22 is supplied to the receiving controllers 28a modified with respect to the receiving controllers 28. During the transmit interval of the signal sequence 24, a switch 31 provided at each receiving controller 28a connects the input of the line 20 to the input on the respective ultrasonic transmitter 10a such that it operates like the ultrasonic transmitter 10 in this phase and radiates an ultrasonic signal 14 towards the material sheet 100. After the end of the signal sequence 24, the switch 31 connects the ultrasonic transmitter 10a to the microcontroller µC+DSP at the receiving controller 28a. Therein, the converted reflection signal 15 is supplied to the microcontroller and the signal processor thereof for evaluation. Concerning the evaluation and the temporal gating of the reflection receive signal, the above described in communication with the measuring unit 2 for evaluation of the transmission signal applies.

Here, the adjustment of the amplification individually programmable for each receiving controller 28a and the calibration are correspondingly applicable, wherein it applies to the reflection signal instead of the transmission signal. If transmission and reflection are measured at the same time, the receiving controllers 28 and 28a operate in parallel as it was described above for the operation of the receiving controllers 28. The results of the evaluated signals or the pre-processed signals are supplied to the main control unit 22 via the line 32a. Programming, control and current supply of the receiving controllers 28a as well as switching of the switches 31 is effected from the main control unit 22 via the control line 30a.

In an embodiment, instead of individual receiving controllers 38a, a group controller can be used, which is configured analogously to the group controller 29 of FIG. 5. The switch 31 can be a controllable switch, which connects the transmitter 10a to the microcontroller/DSP or to the signal line 20 according to control. Or the switch 31 can be a unidirectional direction gate passing signals 24 incoming from the line 20 towards transmitter 10a and supplying returning signals from the transmitter 10a to the microcontroller.

In evaluation or processing of the signals for thickness and/or grammage determination, the quotient of the values of transmission and reflection (T/R) can be used in the calculation in the measuring unit 2a. Via the quotient formation, measurement errors affecting proportionally or approximately proportionally both the transmission and the reflection are cancelled out. Examples of the cause of such measurement errors are the air temperature, air pressure or air humidity.

If thick or highly absorbing materials are measured as the material sheet, the reflection measurement can provide the more accurate results. For example, in transmission, a thickness measurement is unfavorable if the material thickness approaches to $\lambda/4$ of the wavelength of the ultrasonic sound or exceeds this value. In the reflection signal, it is also possible to determine the thickness of the material sheet 100 directly from the propagation time difference of the reflection signal.

The propagation time difference is the difference between the first reflected signal arising upon impinging of the signal 14 on the surface of the material sheet, and the last (without regard to multiple reflections) reflected signal occurring after passage of the signal 14 through the material sheet on the second surface or exit surface. With known sound velocity in the material, then, the material thickness can be directly determined via the propagation time difference determined by means of signal evaluation.

Figure 10:
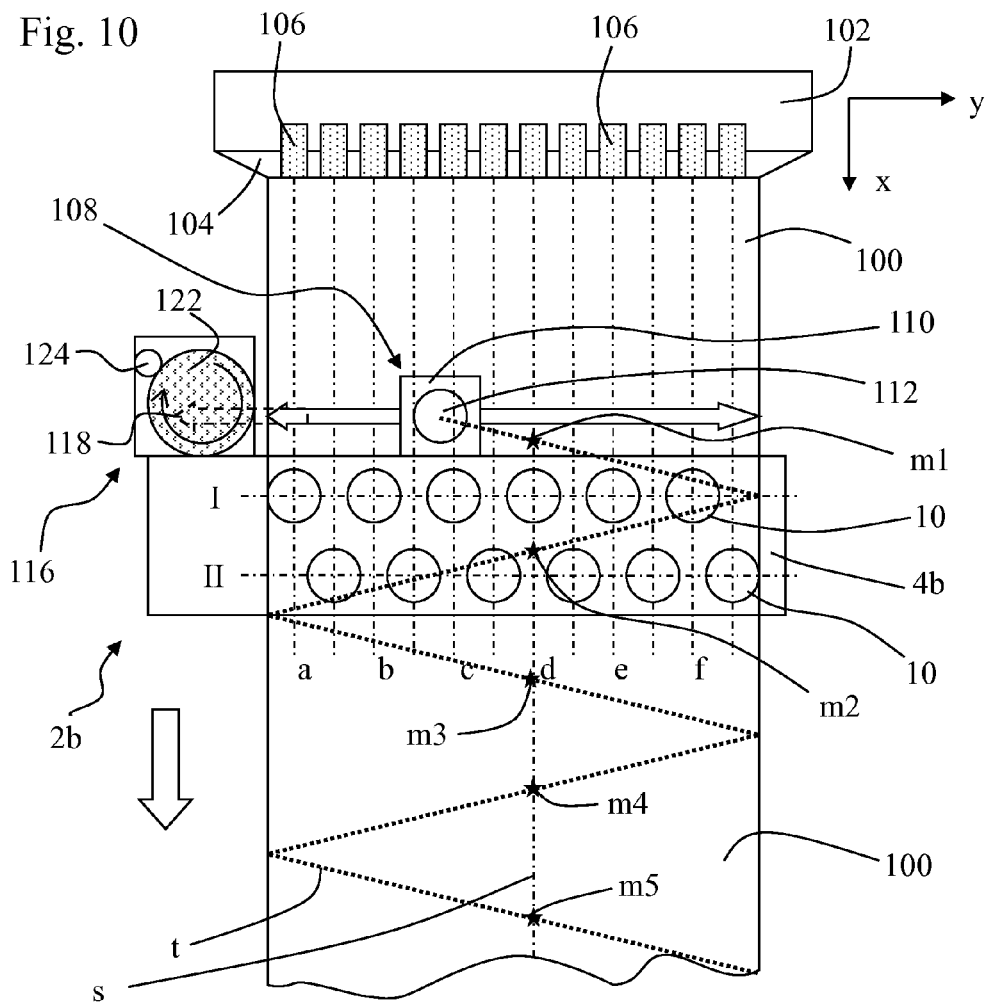
FIG. 10 is a schematic plan view a measuring unit according to further embodiment with a calibration station and a traversing sensor unit in an arrangement with a foil extruder.

FIG. 10 schematically shows in plan view a further configuration of a grammage measuring unit 2b arranged on a material sheet 100 advanced in longitudinal direction x. In the following, the same reference characters are used for the same or equally acting elements as for the above described embodiments of the measuring units 2, 2a. Unless otherwise mentioned, the above explanations also apply to the measuring unit 2b. As above, for simplicity, the transporting device for advancement of the material sheet 100 is not illustrated. The material sheet is directly measured during the manufacturing process with the measuring unit 2b (also 2 or 2a). As illustrated, the material sheet 100 is extruded as a foil through a flat extrusion die 102 of a foil extruder. In FIG. 10 the further elements of the foil extruder are not illustrated—except for the control unit 101 of the extruder in FIG. 11. Instead of the flat extrusion die, a round extrusion die can also be employed for the foil extruder, wherein after extrusion the material sheet is stretched to a flat material sheet in the transport, before it enters the portal 4b of the measuring unit 2b.

As noted above, the grammage measuring unit 2b has a transverse portal 4b as the basic component, which extends above and below the material sheet 100 across the full width of the material sheet. In this case, the transverse portal 4b extends on one side considerably beyond the sheet width, since a standby and calibration station 116 for a traversing or reciprocating measuring group or sensor unit 108 is additionally arranged laterally to the material sheet. On the upper transverse beam of the transverse portal 4b (cf. arrangement of FIG. 3, the beam extending at the top in y direction), a carriage console 110 is supported on a carriage not visible in the figure, wherein the carriage is movable transversely (thus in y direction) to the material sheet 100 in reversing manner by means of a linear drive.

The carriage console 110 supports a transmitting head 112, which can be moved across the full width of the material sheet 100 by means of the carriage console 110. The carriage console 110 supports the transmitting head 112 radiating ultrasonic pulses to the top of the material sheet for measuring. The ultrasonic signal propagates under attenuation through the material sheet 100 to the lower side thereof, where the attenuated ultrasonic signal exits and impinges on a receiving head 114 opposing the transmitting head 112. The receiving head 114 is arranged on a carriage console not illustrated, which in turn is movable on the lower beam of the transverse portal 4b (cf. FIG. 3). The lower carriage with the carriage console for the receiving head 114 is moved synchronously with the upper carriage with the console 110 such that the transmitting head 112 and receiving head 114 of the measuring group 108 oppose each other at any time in moving along the material sheet and in the standby and calibration station 116 (with the material sheet 100 or the calibration sample 122 in between).

At the extrusion die 102, the thickness of the material sheet is adjusted by means of the pivotable die lip 104, wherein the adjustment is effected by means of actuators 106 arranged equidistantly to each other transversely to the sheet width. The actuators 106 are for example thermal expansion bolts, the longitudinal expansion of which is adjustable by temperature variation such that they adjust the work angle of the die lip 104 by the length variation. Therein, each actuator 106 acts locally in its width region such that the thickness of the material sheet in the corresponding y width range is substantially determined by the actuator 106 in this width range or in intermediate ranges between two adjacent actuators 106 by the cooperation of these two actuators.

At the measuring unit 2b, ultrasonic transmitters 10 and ultrasonic receivers 12 paired thereto are arranged over the width of the material sheet on the portal 4b, the common measurement regions of which cover the full width of the material sheet. The arrangement is as described above, wherein here the transmitting block 6 with the transmitters 10 and the receiving block 8 with the receivers 12 are preferably stationary supported on the portal 4b. In this implementation, two array lines I, II offset to each other in transverse direction (y) and six array columns a-f are provided. The above mentioned relating to the transmitters 10 and receivers 12, the electronic control and evaluation thereof (cf. FIGS. 4 and 9) as well as to the procedure of transmitting/receiving/evaluating correspondingly applies.

Figure 11:
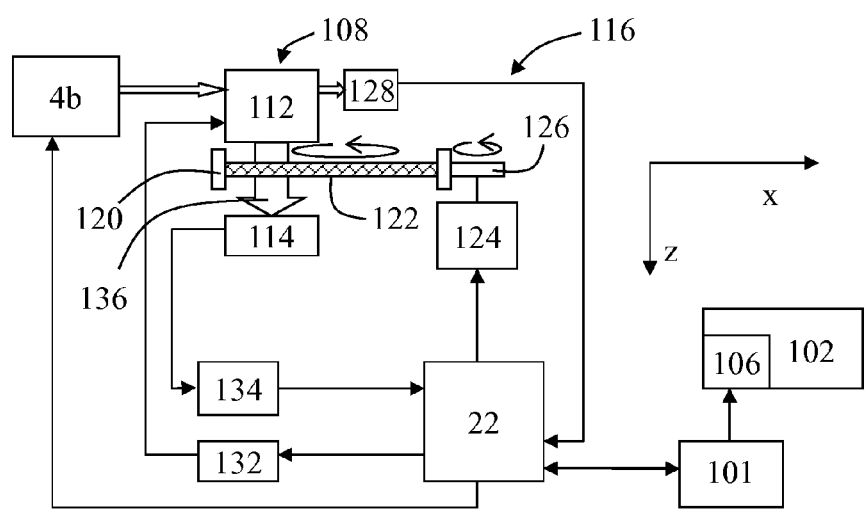
FIG. 11 is a schematic representation of the measuring and control arrangement when positioning the traversing sensor unit in the calibration station of FIG. 10.

As is apparent based on the dot-dashed lines in sheet longitudinal direction (x direction), within the measuring array of the measuring unit 2b one transmitting/receiving pair 10, 12 per actuator 106 is arranged in the longitudinal direction of the sheet 100. The distance of the actuators is in the range of 20 to 40 mm or 25 to 35 mm, typically it is 25.4 or 30 mm. Correspondingly, the center distance of the pairs 10/12 in y direction is equal to the distance of the actuators 106. Here, the association is exemplary from left to right, wherein the transmitting/receiving pair 10/12 in line I and column a is associated with the leftmost actuator 106 and the transmitting/receiving pair 10/12 in line II and column f is associated with the rightmost actuator 106. By this association, it is provided that the measurement results of the layer thickness and/or grammage determination are transmitted from the main control unit 22 to the control unit 101 of the extrusion device as illustrated in FIG. 11. The adjustment of each individual one of the actuators 106 by means of the extruder control unit 101 can then be effected depending on which value of the thickness and/or of the grammage the associated transmitter/receiver pair 10/12 provides. The adjustment of the actuators 106 may be effected continuously and in the form of a feedback control arrangement.

In the schematic cross-sectional view of FIG. 11, the arrangement of transmitting head 112 and receiving head 114 of the measuring group 108 is illustrated in lateral view, wherein the y direction is perpendicular to the drawing plane in FIG. 10 in the lateral view. By 136 an ultrasonic transmission beam is graphically illustrated, which emanates from the transmitting head 112. In the illustrated parking position 118 of the measuring group 108, the transmission beam 136 passes through a calibration sample 122 and impinges on the receiving head 114.

The standby and calibration station 116 is laterally offset to the material sheet, thus offset in y direction or transverse direction to the material sheet 100. The standby and calibration station 116 comprises the parking position 118, in which both the transmitting head 112 and the opposing receiving head 114 are parked during measurement interruptions or for calibration of the measuring group 108 with the transmitting/receiving unit 112, 114.

In the standby and calibration station 116, a clamping ring 120 is rotatably supported, which is set into rotation on its outside by means of a pinion 126. As apparent from FIG. 11, the pinion or gear 126 is driven by a drive motor 124. The pinion 126 engages with a ring gear formed at the outer side of the clamping ring 120 such that the rotating speed or angular position of the clamping ring 120 can be controlled by means of the motor 124. The calibration sample 122 is clamped in the clamping ring 120. The calibration sample 122 is a round blank of a standard material to be employed for calibration. The blank has an area of a square centimeter such that the grammage of the standard can be determined in simple manner by weighing the blank on precision weighing machine. The calibration standard in form of the calibration sample 122 represents a set value for the thickness and/or the grammage of the material sheet 100 and is employed for repeated calibration of the measuring group 108 including the transmitting and receiving heads 112, 114.

FIG. 11 shows the relative position of the calibration sample 122 besides the schematic lateral view of the transmitting and receiving head 112, 114. Similarly, the control and monitoring electronics for the grammage measuring unit 2b relating to the measuring group 108 and calibration station 116 is illustrated in the form of a block diagram. The control of the measuring group 108 and the calibration station 116 is effected by the same main control unit 22, which also provides the control, supply and read-out of the transmitting/receiving units 10/12 of the arrays of the measuring units 2 or 2a. In the unit 2b, the control unit 22 additionally provides the current supply, control, pulse triggering and signal read-out for the measuring group 108 and calibration station 116.

In the standby and calibration station 116, by means of a position sensor 128, it is detected whether the transmitting head 112 and the receiving head 114 have arrived at the correct parking position 118 in order to perform the calibration for example. The position sensor 128 reports its signal to the control unit 22 of the grammage measuring unit 2b.

The control unit 22 controls a transmitter controller 132 of the measuring group 108. For example, the transmitting controller 132 obtains the supply voltage and an amplification adjusting signal for adjusting the signal amplification from the control unit 22. With the preset signal amplification, a pulse signal also received from the control unit 22 for the transmitting head 112 is amplified. The transmitter controller 132 outputs the amplified pulse signal to the transmitting head 112, which converts the voltage signal into the ultrasonic signal 136.

The ultrasonic signal received at the receiving head 114 is converted into an electric signal and supplied to a receiver controller 134. The receiver controller executes signal conditioning and passes the conditioned receive signal to the control unit 22. For example, the receiver controller 134 comprises a digital signal processor, which provides a signal processing algorithm by a corresponding programming via the control unit 22, in order to perform the computationally intensive signal evaluation already on the level of the receiver controller 134.

In order to for example compensate for thermal drifts, ageing processes, contaminants on the transmitting/receiving path of the ultrasonic signal 136 and the like effects, the measurement of the grammage or of the layer thickness of the material sheet 100 is interrupted in presettable or predefined time intervals for calibration. To this, the transmitting and receiving head 112, 114 (group 108) moves laterally out of the measuring section or path (width of the material sheet 100) into the parking position 118. If the correct position of the transmitting and receiving head 112, 114 is detected by means of the position sensor 128, the control unit 22 controls the motor 124 such that the calibration sample 122 clamped in the clamping ring 120 is rotated between transmitting head and receiving head. The center of the transmitting/receiving surface of the transmitting/receiving head 112, 114 is offset radially to the center of the calibration sample 122 such that the center of the transmitting/receiving head is moved relatively to the calibration sample on a circular orbit.

During rotation of the calibration sample 122, ultrasonic transmit pulses are continuously transmitted by the transmitting head 112 and detected by the receiving head 114.

Thereby, the transmission values from the calibration sample 122 are measured at different positions distributed over the surface of the calibrations sample. The measured values are recorded by means of the control unit 22. After one-time or multiple-time rotation of the calibration sample 122, the control unit 22 forms an average from the measured transmission values and uses it to calibrate the calibration curve for the grammage determination or layer thickness determination by the traversing measuring group 108.

FIG. 8 shows exemplarily and schematically with the curve t a calibration curve for the intensity I of the transmission of the ultrasonic signal 136 (cf. signal 14 in FIG. 2) depending on the thickness d (the same also applies to the grammage) of the material sheet 100. If the averaging of the previously described determined transmission measurement results in a deviating calibration value for the layer thickness d or the grammage, thus, the calibration curve is correspondingly upwardly or downwardly corrected.

Thereby, a newly calibrated calibration curve is available after the calibration and the layer thickness measurement by means of the measuring group 108 transversely to the material sheet 100 can be continued with the new calibration curve such that the grammage or layer thickness determinations can be performed with higher reliability.

As illustrated in the configuration of the measuring unit 2b in FIG. 10, the measuring unit includes both the traversing measuring group 108 (i.e. reciprocating across the material sheet 100) as well as the stationary array with the (here twelve) transmitting/receiving pairs 10/12. The measuring group 108 is absolutely calibrated in the calibration station 116 by means of the sample 122. The calibrated measuring group 108 is then used to calibrate the transmitting/receiving pairs 10/12 as follows. The cooperation of material sheet 100 moved in longitudinal direction x and measuring group 108 reciprocating in transverse direction y results in the zigzag-shaped sampling path t illustrated dotted in FIG. 10.

Along the sampling path t, the measuring group 108 detects measurement values of the layer thickness and/or the grammage with the repetition rate of the pulsed measurement (cf. FIG. 6). Therein, the path t also sweeps the center of the measurement region of the transmitting/receiving pairs 10/12 extending in the longitudinal direction x, which is exemplarily illustrated dot-dashed with line s for the pair 10/12 in line I, column d (in the following referred to as "(I, d) pair 10/12"). For this example, the five measurement points m1 to m5 are the crossing points of the crossing measuring lines or paths s and t. For calibration of this (I, d) pair 10/12, for example, the average of the five measurement points m1 - m5 for the thickness and/or the grammage each for the measurement by means of the measuring group 108 and the measurement by means of the (I, d) pair 10/12 is formed, and if they deviate from each other, the calibration value for the (I, d) pair 10/12 is newly set such that the averaged values for the measurement points m1 to m5 between measuring group 108 and (I, d) pair 10/12 coincide. At least, the new calibration value is used in the following measurements for the (I, d) pair 10/12 until it again has been calibrated against the measuring group 108. In this manner, the other transmitting/receiving pairs 10/12 are calibrated with the corresponding measurement values on the crossing points of the sampling path t and the associated measuring line s of the transmitting/receiving pair 10/12 extending in x direction. This represents a relative calibration of the transmitting/receiving pairs 10/12 against the measuring group 108.

The feedback of the measurement value of the layer thickness or the grammage of the material sheet from the transmitting/receiving pairs 10/12 via the control unit 22 and the control unit 101 for adjusting the actuators 106 on the extrusion die 102 allows a substantially faster control as if for example only the reversing measuring group 108 would be used for measuring and controlling. Moreover, in the measurement at the material sheet 100 and when using only the reversing measuring group 108 it is not possible to identify whether a thickness variation in the longitudinal profile (direction x) or transverse profile (direction y) of the sheet 100 has occurred. A thickness variation in the longitudinal profile for example occurs if the sheet transport proceeds unstably or the foil material exits the die 102 non-uniformly (e.g. on the whole width) due to pressure variations in the extruder. A thickness variation in the transverse profile for example occurs if an individual actuator 106 operates non-uniformly or differently or the die 102 is locally occluded at one or more of the actuators.

In an embodiment, in the measuring unit 2b too, the transmitting heads 112 and opposing the receiving heads 114 can be arranged on a transmitting block 6 and receiving block 8 y-displaceable synchronously with each other as in the measuring unit 2a.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. An arrangement comprising an ultrasonic transmitting and receiving device and a foil extruder having at least one extrusion die, wherein the ultrasonic transmitting and receiving device is configured for measuring the transmission (T) and/or the reflection (R) of ultrasonic waves on a thin material sheet for determining the layer thickness and/or the grammage of the material sheet, the arrangement comprises:
 a plurality of ultrasonic transmitters;
 a plurality of ultrasonic receivers, wherein the number of the ultrasonic receivers corresponds to the number or the two-fold number of the ultrasonic transmitters; and
 one receiver electronics respectively for each of the ultrasonic receivers or a group receiver electronics respectively for a predetermined number of ultrasonic receivers;
 wherein at least one actuator is assigned to the extrusion die for adjusting the foil thickness,
 wherein the foil extruder comprises a control unit for adjusting or altering the at least one actuator,
 wherein the control unit receives at least one measurement value for the layer thickness and/or the grammage from the ultrasonic transmitting and receiving device, or from a control unit of the ultrasonic transmitting and receiving device, and
 wherein the control unit adjusts or alters the at least one actuator depending on the at least one measurement value.

2. The arrangement according to claim 1, wherein the ultrasonic transmitting and receiving device is arranged parallel to a thin material sheet which is to be measured and which is movable in longitudinal direction, wherein the ultrasonic transmitters are distributed on a supporting device, wherein the supporting device extends perpendicularly or substantially perpendicularly to the longitudinal direction (thus in transverse direction y) of the movable material sheet.

3. The arrangement according to claim 1, wherein the ultrasonic transmitters are spatially distributed both over the transverse direction (y) of the material sheet and over a predetermined depth in the longitudinal direction (x) of the movable material sheet.

4. The arrangement according to claim 1, comprising multiple lines of the ultrasonic transmitters extending in transverse direction (y) and all of the ultrasonic transmitters are offset to each other in transverse direction (y), wherein the ultrasonic transmitters of all of the lines are arranged equidistantly to each other in transverse direction (y) in projection in longitudinal direction (x).

5. The arrangement according to claim 1, comprising multiple lines of the ultrasonic transmitters extending in transverse direction (y) and all of the ultrasonic transmitters are offset to each other in transverse direction (y), wherein in projection in longitudinal direction (x), the ultrasonic transmitters is a repeating permutation of the lines in transverse direction.

6. The arrangement according to claim 5, wherein in particular the ultrasonic transmitters of all of the lines are arranged equidistantly to each other in transverse direction (y) in projection in longitudinal direction (x).

7. The arrangement according to claim 1, wherein the radiation direction of the ultrasonic transmitters is oriented towards the surface of the material sheet perpendicularly or approximately perpendicularly to the surface of the material sheet, and wherein the respective ultrasonic receiver associated with the ultrasonic transmitter is arranged in transmission direction of the ultrasonic transmitter after transmission through the material sheet and/or in reflection direction after the reflection at the material sheet.

8. The arrangement according to claim 1, wherein the ultrasonic receivers are arranged on a second supporting device paired to the arrangement of the ultrasonic transmitters, wherein the second supporting device is arranged at the side of the material sheet opposing the supporting device.

9. The arrangement according to claim 1, wherein each of the receiver electronics or group receiver electronics comprises an amplifier in which the amplification is adjustable, in multiple amplification stages.

10. The arrangement according to claim 9, wherein each of the receiver electronics comprises a signal processor for evaluating the signal received from the associated ultrasonic receiver, wherein the signal processor is implemented in the microcontroller.

11. The arrangement according to claim 1, comprising a main control unit for generating a transmit signal, wherein the main control unit is connected to each of the ultrasonic transmitters and supplies the transmit signal to each of the ultrasonic transmitters, wherein the transmit signal is supplied to all of the ultrasonic transmitters at the same time or with slight temporal offset.

12. The arrangement according to claim 1, further comprising a measuring group or sensor unit with a transmitting head and a receiving head, which is movable transversely (y) to the material sheet on a portal of the device for thickness measurement and/or grammage measurement.

13. The arrangement according to claim 12,
 wherein a calibration station is assigned to the measuring group or sensor unit, at which the measuring group or sensor unit is configured to be calibrated by means of a calibration sample.

14. The arrangement according to claim 12,
wherein each of the ultrasonic transmitter and receiver pairs is configured to be calibrated by means of a control unit of the device by evaluation of the measurement results (m1 ... 5, t) of the measuring group or sensor unit measured at the material sheet and the measurement results (m1 ... m5, s) of the ultrasonic transmitter and receiver pairs measured at the material sheet.

15. The arrangement according to claim 1, wherein a plurality of actuators is arranged at the extrusion die and an ultrasonic transmitter and receiver pair or each one group of ultrasonic transmitter and receiver pairs is associated with each actuator or a group of actuators is associated with each one ultrasonic transmitter and receiver pair, wherein the control unit adjusts or alters an actuator or a group of actuators depending on the measurement signal or the measurement signals from the associated ultrasonic transmitter and receiver pair or the group of the ultrasonic transmitter and receiver pairs.

16. A method for ultrasonic transmission measurement and/or ultrasonic absorption measurement for thickness and/or grammage determination at a material sheet, the method comprising:
providing a plurality of ultrasonic transmitters arranged distributed planar on a supporting device both in transverse direction (y) and in longitudinal direction (x) of the material sheet to be measured;
providing a plurality of ultrasonic receivers, wherein the number of the ultrasonic receivers corresponds to the number or the two-fold number of the ultrasonic transmitters and wherein each one or two ultrasonic receivers are associated with one of the ultrasonic transmitters, and the receiving surface of the ultrasonic receiver is oriented such that it receives either the transmission (T) of the ultrasonic signal emitted by the associated ultrasonic transmitter after transmission through the material sheet or the reflection (R) of the signal reflected from the material sheet;
providing one receiver electronics respectively for each of the ultrasonic receivers or a group receiver electronics respectively for a predetermined number of ultrasonic receivers;
supplying a control signal to all of the ultrasonic transmitters, wherein the supply is effected such that all of the ultrasonic transmitters emit an ultrasonic signal at the same time or substantially at the same time or all of the signals of the ultrasonic transmitters are emitted within a time window, wherein the length of the time window is smaller than the propagation time of a spurious reflection signal and/or the signal of an ultrasonic transmitter not associated with the receiver;
parallel or substantially parallel processing of the signal received from the ultrasonic receiver by means of the receiver electronics or group receiver electronics; and
forwarding the processing results to a main control device,
wherein the thickness and/or grammage determination is executed by the main control unit after forwarding the processing results or is executed in the receiver electronics or the group receiver electronics by parallel processing.

17. The method according to claim 16, wherein each of the sensor units comprising the ultrasonic receiver and the ultrasonic transmitter is calibrated by:
for each of the sensor units, adjusting an amplification factor in the receiver electronics associated with the ultrasonic receiver or the group receiver electronics based on a signal transmitted through air with material sheet not present.

18. The method according to claim 16, wherein each of the sensor units comprising the ultrasonic receiver and the ultrasonic transmitter is calibrated by:
for each of the sensor units, adjusting a material calibration value based on a transmission or reflection signal from a calibration sample for the material sheet to be measured.

19. The method according to claim 18, wherein each of the sensor units comprising the ultrasonic receiver and the ultrasonic transmitter is calibrated by:
for each of the ultrasonic receiver or the group receiver electronics based on a signal transmitted through air with material sheet not present.

\* \* \* \* \*